United States Patent

Sugimori et al.

Patent Number: 4,477,369
Date of Patent: Oct. 16, 1984

[54] NEW HIGH TEMPERATURE LIQUID-CRYSTALLINE SUBSTANCES CONSISTING OF 4 OR 5 SIX-MEMBER-RINGS AND LIQUID-CRYSTALLINE COMPOSITIONS CONTAINING SAME

[75] Inventors: Shigeru Sugimori; Tetsuhiko Kojima, both of Kanagawaken, Japan

[73] Assignee: Chisso Corporation, Osaka, Japan

[21] Appl. No.: 460,071

[22] Filed: Jan. 21, 1983

[30] Foreign Application Priority Data

| Jan. 22, 1982 | [JP] | Japan | 57-8291 |
| Feb. 16, 1982 | [JP] | Japan | 57-23438 |
| Mar. 8, 1982 | [JP] | Japan | 57-36100 |
| Apr. 1, 1982 | [JP] | Japan | 57-54080 |
| Apr. 1, 1982 | [JP] | Japan | 57-54081 |
| May 10, 1982 | [JP] | Japan | 57-77928 |
| May 20, 1982 | [JP] | Japan | 57-85272 |
| Jul. 2, 1982 | [JP] | Japan | 57-115181 |
| Jul. 2, 1982 | [JP] | Japan | 57-115182 |

[51] Int. Cl.³ ............ C09K 3/34; G02F 1/13; C07C 13/28; C07C 43/21; C07C 43/215; C07C 43/184; C07C 35/21; C07C 25/18; C07C 49/613

[52] U.S. Cl. .............. 252/299.6; 252/299.5; 252/299.63; 252/299.66; 350/350 R; 350/350 S; 568/631; 568/642; 568/643; 568/644; 568/659; 568/660; 568/664; 585/20; 585/23; 585/25

[58] Field of Search ........... 252/299.5, 299.63, 299.66, 252/299.6; 585/20, 23, 25; 568/642, 643, 644, 631, 659, 660, 664; 350/350 R, 350 S

[56] References Cited

U.S. PATENT DOCUMENTS

| 4,330,426 | 5/1982 | Eidenschink et al. | 252/299.63 |
| 4,331,552 | 5/1982 | Eidenschink et al. | 252/299.63 |
| 4,405,488 | 9/1983 | Sugimori et al. | 252/299.63 |
| 4,439,340 | 3/1984 | Kojima et al. | 252/299.63 |

FOREIGN PATENT DOCUMENTS

| 62470 | 10/1982 | European Pat. Off. | 252/299.63 |
| 3223637 | 1/1983 | Fed. Rep. of Germany | 252/299.63 |
| 57-49688 | 3/1982 | Japan | 252/299.63 |
| 57-158729 | 9/1982 | Japan | 252/299.63 |
| 58-38221 | 3/1983 | Japan | 252/299.63 |

OTHER PUBLICATIONS

Detar, D. F. et al., J. Am. Chem. Soc., vol. 89, No. 16, pp. 4051-4057 (Aug. 2, 1967).
Hawkes, G. E. et al., J. Chem. Soc. Perkin Trans. II, pp. 1709-1716 (1976).
Eidenschink, R. Mol. Cryst. Liq. Cryst., vol. 94, pp. 119-125 (1983).
Demus, D. et al., Flüssige Kristalle in Tabellen, pp. 230-232 & 34-35 (1975).
Billard, J. et al., Mol. Cryst. Liq. Cryst., vol. 41 (Lett.), pp. 217-222 (1978).

Primary Examiner—Teddy S. Gron
Attorney, Agent, or Firm—Fred Philpitt

[57] ABSTRACT

Liquid-crystalline compounds which exhibit a liquid crystalline phase within a broader temperature range and also have a high transparent point and yet a low viscosity, and liquid-crystalline compositions containing at least one kind of the above compounds are provided, which compounds are high temperature liquid-crystalline substances consisting of 4 or 5 six-member-rings, expressed by the general formula

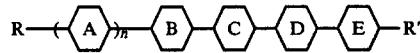

wherein R and R' each represent hydrogen atom or an alkyl group or an alkoxy group, each having 1 to 10 carbon atoms;

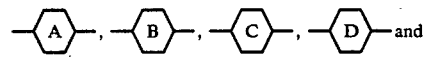

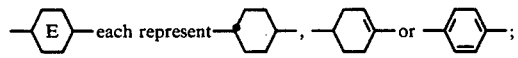

and n represents 0 or 1.

20 Claims, No Drawings

NEW HIGH TEMPERATURE LIQUID-CRYSTALLINE SUBSTANCES CONSISTING OF 4 OR 5 SIX-MEMBER-RINGS AND LIQUID-CRYSTALLINE COMPOSITIONS CONTAINING SAME

BACKGROUND OF THE INVENTION

1. Field of the Invention

This invention relates to new liquid-crystalline substances which exhibit a liquid-crystalline phase in a broad temperature range, and compositions containing the same.

2. Description of the Prior Art

Display elements using liquid crystals have come to be widely used for watches, desk calculators, etc. Such liquid-crystalline display elements utilize optical anisotropy and dielectric anisotropy of liquid-crystalline substances, and their liquid-crystalline phases include nematic liquid-crystalline phase, smectic liquid-crystalline phase and cholesteric liquid-crystalline phase, and those utilizing nematic liquid crystals among them have been most broadly employed for practical uses. Further, liquid-crystalline display elements include those of TN type (twisted nematic type), DS type (dynamic scattering type), guest-host type, DAP type, etc. and properties required for liquid-crystalline substances used therefor are varied. At any rate, however, as liquid-crystalline substances used for these display elements, those which exhibit a liquid-crystalline phase within as broad a range as possible in the natural world have been desired. However, no single compounds satisfying such a requirement have been found to date, and it is the present status that liquid-crystalline compositions which are practically usable for the present have been obtained by mixing together several kinds of liquid-crystalline compounds or non-liquid-crystalline compounds. Further, these substances, of course, must be stable to moisture, heat, air, etc., and moreover, it has been desired for the substances that the threshold voltage and saturation voltage required for driving the display elements be as low as possible and the viscosity be as low as possible for making the response speed higher. Further, for broadening the liquid-crystalline temperature range toward the higher temperatures, it is necessary to employ a high melting liquid-crystalline substance as a component, but such a high melting liquid-crystalline substance generally has a high viscosity and accordingly a liquid-crystalline composition containing it also has a high viscosity; hence there has been a tendency that the response speed of liquid-crystalline display elements as usable up to e.g. 80° C., particularly that at lower temperatures, becomes notably slow.

The present inventors previously invented 1-alkyl-4-[trans-4-(trans-4-alkylcyclohexyl)cyclohexyl]benzenes expressed by the general formula

as one of liquid-crystalline compounds improving the low temperature characteristic, and filed a patent application claiming the same (Japanese patent application laid-open No.Sho 57-165,328/1982).

However, recent technical advance of liquid-crystalline display elements has been so remarkable that display elements being actuated at a temperature ranging from a further lower temperature to a higher temperature have been required.

The object of the present invention is to provide a liquid-crystalline compound corresponding to such a requirement, that is, exhibiting a liquid-crystalline phase within a broader temprature range and also having a high transparent point and yet a low viscosity.

SUMMARY OF THE INVENTION

The present invention resides in:

novel high temperature liquid-crystalline substances consisting of 4 or 5 six-member-rings, expressed by the general formula

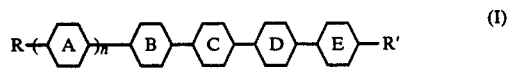 (I)

wherein R and R' represent hydrogen atom or an alkyl group or an alkoxy group each having 1 to 10 carbon atoms, respectively;

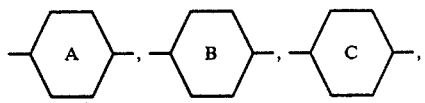

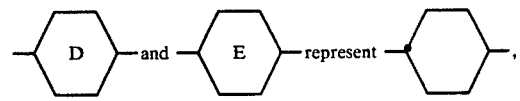

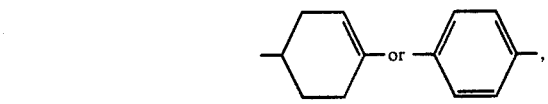

respectively; and n represents 0 or 1, and liquid-crystalline compositions containing at least one kind of said liquid-crystalline substances.

DETAILED DESCRIPTION OF THE INVENTION

The compounds of the present invention not only have a broad liquid-crystalline temperature range, but also exhibit a liquid-crystalline phase up to high temperatures such that the liquid-crystalline-transparent points are in the vicinity of 300° C., and nevertheless have a relatively low viscosity, and yet, when they are mixed in a small amount with other liquid-crystalline compounds such as ester, biphenyl, phenylcyclohexane, Schiff or azoxy liquid-crystalline compounds, hetero-ring-containing liquid-crystalline compounds, etc., they are very useful as a liquid-crystalline component to be used in a cell for liquid-crystalline display elements being actuated in a broad range of from low temperature to high temperature. Further, the compounds of the present invention are so high in the liquid-crystalline-transparent point that addition thereof in a small amount may be sufficient; hence the threshold voltage and the saturation voltage of the liquid-crystalline compositions obtained by adding the compounds of the present invention do not rise so high as compared with those of the compositions without the compounds of the present invention, but are almost the same as those of the latters. Further the compounds of the present invention are stable to light, heat, air, moisture, etc. and have a very broad application range.

Concrete examples of preferable compounds among those of the formula (I) are the following compounds having general formulas (II) to (X):

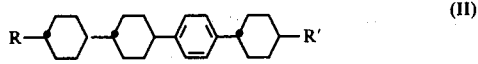  (II)

wherein R and R' represent hydrogen atom or an alkyl group of 1 to 10 carbon atoms, respectively;

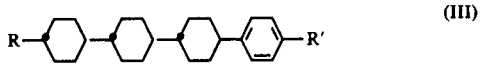  (III)

wherein R and R' represent hydrogen atom or an alkyl group or an alkoxy group, each of 1 to 10 carbon atoms, respectively;

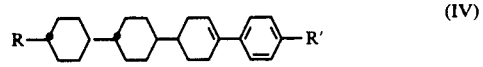  (IV)

wherein R and R' represent hydrogen atom or an alkyl group or an alkoxy group, each of 1 to 10 carbon atoms, respectively;

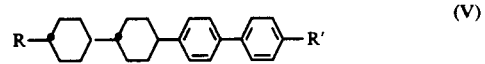  (V)

wherein R and R' represent hydrogen atom or an alkyl group or an alkoxy group, each of 1 to 10 carbon atoms, respectively;

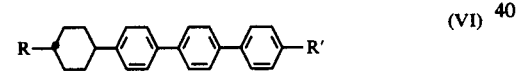  (VI)

wherein R and R' represent hydrogen atom or an alkyl group or an alkoxy group, each of 1 to 10 carbon atoms, respectively;

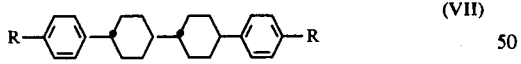  (VII)

wherein R represents hydrogen atom or an alkyl group or an alkoxy group, each of 1 to 10 carbon atoms;

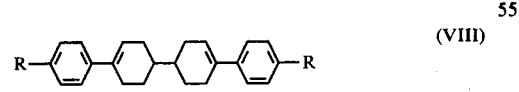  (VIII)

wherein R represents hydrogen atom or an alkyl group or an alkoxy group, each of 1 to 10 carbon atoms;

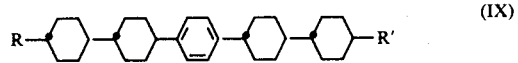  (IX)

wherein R and R' represent hydrogen atom or an alkyl group of 1 to 10 carbon atoms, respectively; and

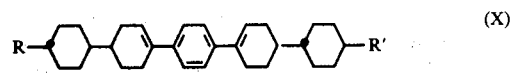  (X)

wherein R and R' represent hydrogen atom or an alkyl group of 1 to 10 carbon atoms, respectively. Next, the preparations of the compounds of the present invention will be described.

Preparation of compounds of the formula (II)

First, from p-dibromobenzene and metallic magnesium is prepared 4-bromobenzenemagnesium bromide, which is then reacted with a 4-alkylcyclohexanone to obtain a 4-(4'-alkylcyclohexan-1-ol)bromobenzene, which is then dehydrated in the presence of potassium hydrogen sulfate as catalyst to obtain a 4-(4'-alkylcyclohexen-1-yl)bromobenzene, which is then converted with metallic magnesium into a 4-(4'-alkylcyclohexen-1-yl)benzenemagnesium bromide, which is then subjected to catalytic reduction in an autoclave in the presence of a Raney Ni as catalyst, followed by recrystallization, to obtain an objective product, a 1-(trans-4-alkylcyclohexyl)-4-[trans-4-(trans-4-alkylcyclohexyl)cyclohexyl]benzene (II). The above steps are expressed by the following equations:

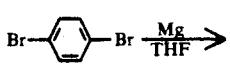

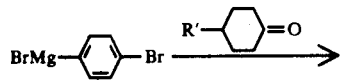

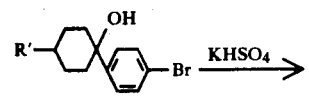

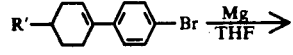

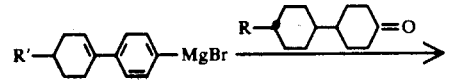

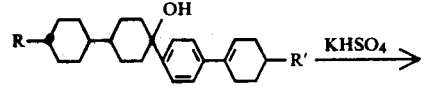

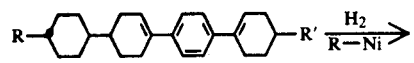

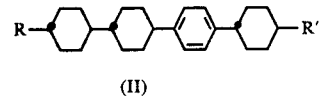

(II)

Preparation of compounds of the formulas (V) and (VI)

Metallic Mg is reacted with a 4-substituted-4'-bromobiphenyl to obtain a 4-substituted-4'-biphenylmagnesium bromide, which is then reacted with a 4-(trans-4-substituted-cyclohexyl)cyclohexanone to obtain a 4-substituted-4'-[4-(trans-4-substituted-cyclohexyl)cyclohexan-1-ol]biphenyl, which is then dehydrated in the presence of potassium hydrogen sulfate as catalyst to obtain a 4-substituted-4'-[4-(trans-4-substituted-cyclohexyl)cyclohexen-1-yl]biphenyl (XI), which is then reduced under oridinary pressure at 50° C. using Raney Ni catalyst in n-heptane solvent, followed by removing a cis-form substance by recrystallization to obtain an objective product, a 4-substituted-4'-[trans-4-(trans-4-substituted-cyclohexyl)cyclohexyl]biphenyl (V).

The above steps are expressed by the following equations:

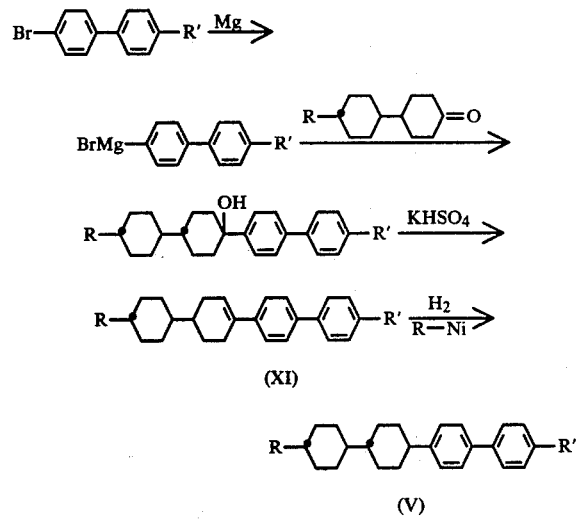

(XI)

(V)

The above compounds (V) are also obtained according the following method:

Metallic Mg is reacted with 4-bromobiphenyl to obtain 4-biphenylmagnesium bromide, which is then reacted with a 4-(trans-4-substituted-cyclohexyl)cyclohexanone to obtain a 4-[4-trans-4-substituted-cyclohexyl)cyclohexan-1-ol]biphenyl, which is then dehydrated with potassium hydrogen sulfate to obtain a 4-[4-(trans-4-substituted-cyclohexyl)cyclohexen-1-yl]biphenyl, which is then reduced with Raney Ni catalyst to obtain 4-[trans-4-(trasns-4-substituted-cyclohexyl)cyclohexyl]biphenyl, which is then subjected to Friedel-Krafts reaction with aluminium chloride and an alkanoyl chloride to obtain a 4-alkanoyl-4'-[trans-4-(trans-4-substituted-cyclohexyl)cyclohexyl]biphenyl, which is then subjected to Wolff-Kishner reduction to obtain an objective product (V).

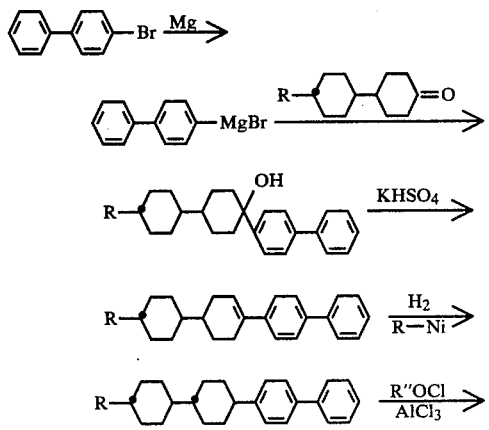

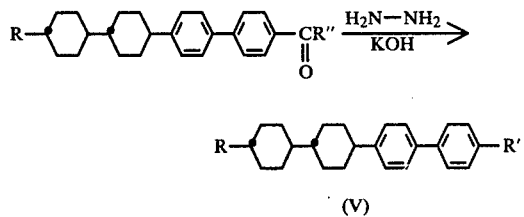

(V)

Preparation of compounds of the formula (VI)

A compound of the formula (XI) in the preparation of the compounds of the formula (V) is dehydrogenated with chloranil to obtain an objective product, a 4-substituted-4'-(trans-4-alkylcyclohexyl)terphenyl. The above step is expressed by the following chemical equation:

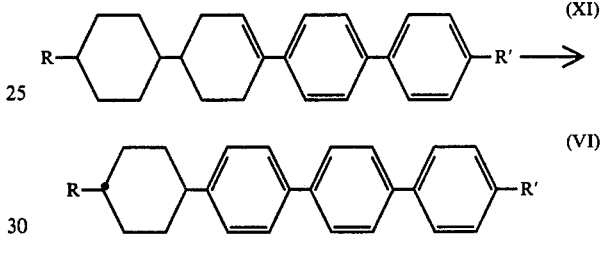

Preparation of compounds of the formulas (III) and (IV)

Metallic Mg is reacted with 4-methoxy-bromobenzene to obtain 4-methoxybenzenemagnesium bromide, which is then reacted with a 4-(trans-4-alkylcyclohexyl)cyclohexanone to obtain a 4-methoxy-[4-(trans-4-alkylcyclohexyl)cyclohexen-1-ol]benzene, which is then dehydrated to obtain a 4-methoxy-[4-(trans-4-alkylcyclohexyl)cyclohexen-1-yl]benzene, which is then reduced with Raney Ni catalyst, followed by recrystallization to obtain a 4-methoxy-[trans-4-(trans-4-alkylcyclohexyl)cyclohexyl]benzene, which is then subjected to demethylation reaction with hydrobromic acid to obtain a 4-hydroxy-[trans-4-(trans-4-alkylcyclohexyl)cyclohexyl]benzene, which is then subjected to catalytic reduction under 50 kg/cm² at 150° C. with Ru/C catalyst to obtain a 4-[trans-4-(trans-4-alkylcyclohexyl)cyclohexyl]cyclohexanol, which is then subjected to oxidation reaction with a mixed solution of chromic acid-sulfuric acid to obtain a 4-[trans-4-(trans-4-alkylcyclohexyl)cyclohexyl]cyclohexanone (XII), which is then dropwise added to a Grignard reagent obtained by reacting a 4-substituted-bromobenzene with Mg, to obtain a 4-substituted-1-{4-[trans-4-(trans-4-alkylcyclohexyl)cyclohexyl]cyclohexan-1-ol}benzene, which is then dehydrated to obtain a 4-substituted-{4-[trans-4-(trans-4-alkylcyclohexyl)cyclohexyl]cyclohexen-1-yl}benzene (IV), which is then reduced with Raney Ni catalyst, followed by recrystallization to obtain an objective product, a 4-substituted-{trans-4-[trans-4-(trans-4-alkylcyclohexyl)cyclohexyl]cyclohexyl}benzene (III). The above steps are expressed by the following chemical equations:

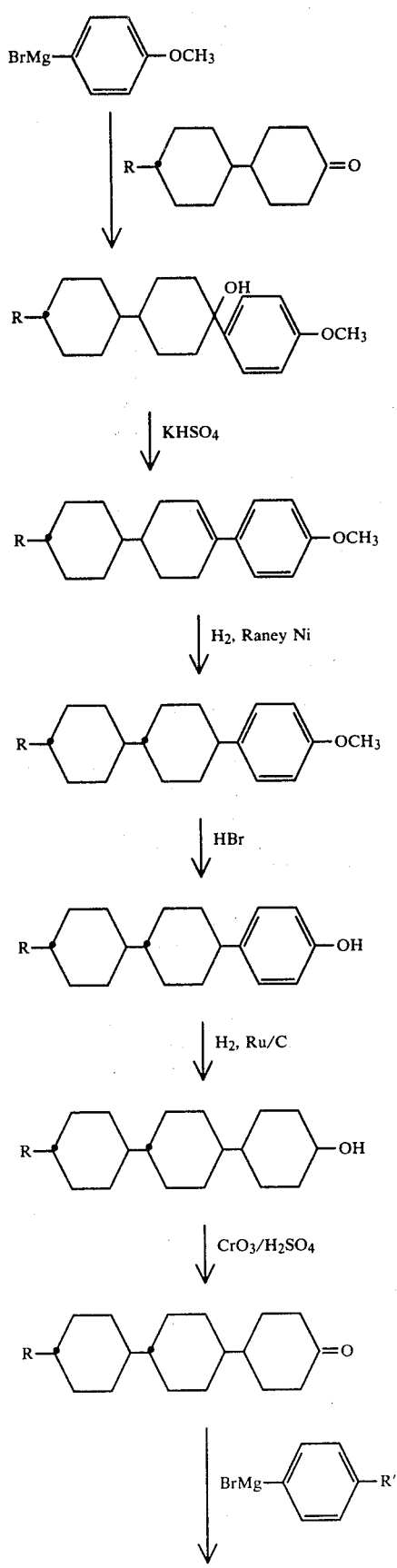

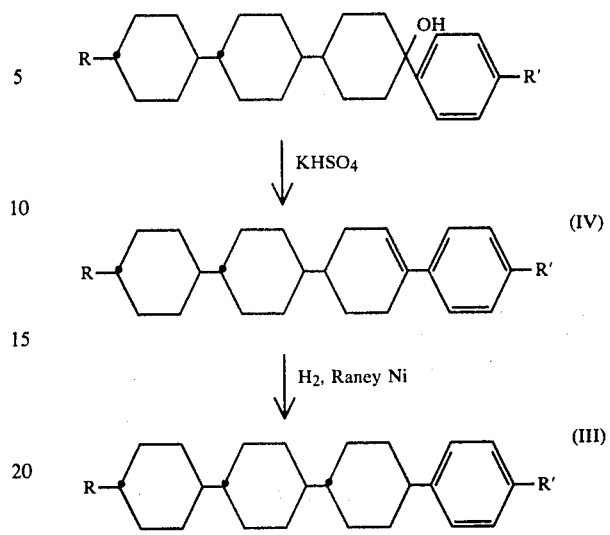

Preparation of compounds of the formulas (VII) and (VIII)

Metallic magnesium is reacted with a 4-substituted-bromobenzene to obtain a 4-substituted-phenylmagnesium bromide, which is then reacted with 4,4'-bicyclohexanedione to obtain a 4,4'-bis(4-substituted-phenyl)bicyclohexan-4,4'-diol, which is then dehydrated with potassium hydrogen sulfate catalyst to obtain a 4,4'-bis(4-substituted-phenyl)bicyclohexan-3,3'-diene (VIII), which is then subjected to catalytic reduction in an autoclave with Raney Ni catalyst, followed by recrystallization to obtain an objective product, a trans, trans-4,4'-(4-substituted-phenyl)bicyclohexane (VII).

The above steps are expressed by the following chemical equations:

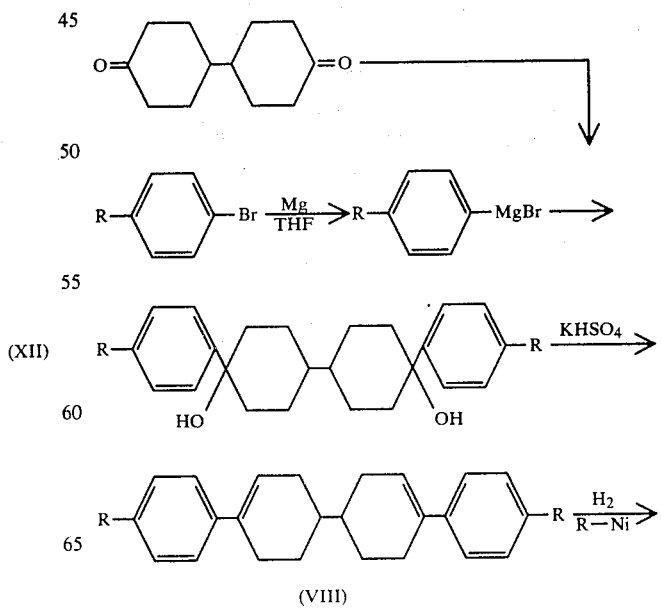

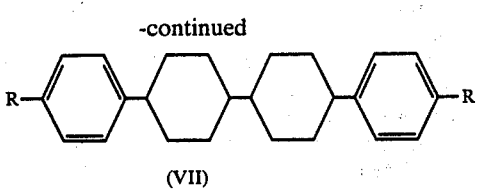

(VII)

Preparation of compounds of the formulas (IX) and (X)

Metallic magnesium is reacted with p-dibromobenzene to obtain p-phenyldimagnesium bromide, which is then reacted with a 4-(trans-4-substituted-cyclohexyl)-cyclohexanone to obtain a 1,4-bis[4-(trans-4-alkylcyclohexyl)cyclohexan-1-ol]benzene, which is then dehydrated with potassium hydrogen sulfate catalyst to obtain a 1,4-bis[4-(trans-4-alkylcyclohexyl)cyclohexen-1-yl]benzene (X), which is then reduced with Raney Ni to obtain an objective product, a 1,4-bis[trans-4-(trans-4-alkylcyclohexyl]benzene (IX). The above steps are expressed by the following chemical equations:

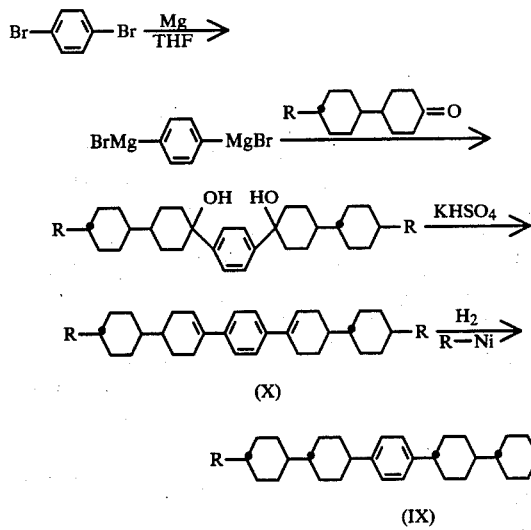

The compounds of the present invention will be further described by way of Examples in more detail.

EXAMPLE 1

Preparation of 1-(trans-4-methylcyclohexyl)-4-[trans-4-(trans-4-pentylcyclohexyl)cyclohexyl]-benzene (a compound of the general formula (II) wherein $R=C_3H_7$ and $R'=CH_3$). Sliced magnesium (29.2 g, 1.20 mol) was placed in a three-neck flask, and a solution obtained by dissolving p-dibromobenzene (283.1 g, 1.20 mol) in tetrahydrofuran (500 ml) was slowly dropwise added to the magnesium in nitrogen current with stirring while the reaction temperature was kept at 30°–35° C. After 3 hours, the reaction was completed to form its magnesium bromide, to which a solution obtained by dissolving 4-methylcyclohexanone (107.1 g, 1.00 mol) in tetrahydrofuran (200 ml) was rapidly dropwise added while the reaction temperature was kept at 30° C. or lower. After the addition, the mixture was refluxed for 20 minutes and 3-N hydrochloric acid was then added. The reaction liquid was extracted with n-heptane (three times, 300 ml) and the n-heptane layers were combined together and washed with water, followed by distilling off the solvent under reduced pressure. The residual oily substance was 4-(4-methylcyclohexan-1-ol)bromobenzene, to which potassium hydrogen sulfate (30 g) was added, followed by dehydration at 200° C. for 2 hours in nitrogen current. After cooling, n-heptane (1 l) was added and potassium hydrogen sulfate was filtered off, followed by washing the n-heptane layer with water and distilling off the solvent under reduced pressure. The residue was distilled under reduced pressure and main fractions (170°~173° C./9 mmHg) were collected, followed by recrystallization from ethanol to obtain 4-(4-methylcyclohexen-1-yl)bromobenzene. This bromobenzene (6.1 g, 0.024 mol) was dissolved in tetrahydrofuran (20 ml) and reacted with metallic magnesium (0.58 g, 0.024 mol) in nitrogen current to obtain 4-(4-methylcyclohexen-1-yl)benzenemagnesium bromide, to which a solution obtained by dissolving 4-(trans-4-pentylcyclohexyl)cyclohexanone (4.8 g, 0.019 mol) in tetrahydrofuran (20 ml) was added, followed by extracting with n-heptane (300 ml), washing the oily layer with water and distilling off the solvent under reduced pressure. Potassium hydrogen sulfate (2 g) was added to the residue, followed by dehydration at 200° C. for 2 hours in nitrogen current. After cooling, toluene (200 ml) was added, potassium hydrogen sulfate was filtered off and the toluene layer was washed with water. The solvent was distilled off under reduced pressure and the residue was recrystallized from toluene to obtain 1-(4'-methylcyclohexen-1-yl)-4-[4-(trans-4-pentylcyclohexyl)cyclohexen-1-yl]benzene. This material (1.2 g) was dissolved in toluene (20 ml), and Raney Ni (1.0 g) was added, followed by catalytic reduction in an autoclave. The reaction was traced by gas chromatography and when the raw material disappeared, the catalyst was filtered off and recrystallization was repeated to isolate an objective product, 1-(trans-4-methylcyclohexyl)-4-[trans-4-(trans-4-pentylcyclohexyl)-cyclohexyl]benzene (yield: 0.1 g). This product had a crystalline-smectic point (C-Sm point) of 30° C. or lower, a smectic-nematic point (Sm-N point) of 256° C. and a nematic-transparent point (N-I point) of 259° C.

EXAMPLES 2–5

Various compounds having different substituents were prepared in the same manner as in Example 1. They are shown in Table 1 together with the results of Example 1.

In addition their chemical structures were confirmed by way of NMR, etc.

TABLE 1

| | In formula (II) | | Yield | Phase transition point (°C.) | | |
|---|---|---|---|---|---|---|
| Example | R | R' | (g) | C-sm point | Sm-N point | N-I point |
| 2 | $C_3H_7$ | $CH_3$ | 0.1 | 30 or lower | — | 300 or higher (Sm-I) |
| 3 | $C_3H_7$ | $C_2H_5$ | 0.2 | 30 or lower | 274 | 287 |
| 4 | $C_3H_7$ | $C_3H_7$ | 0.5 | 55 | 264 | 300 or higher |
| 1 | $C_5H_{11}$ | $CH_3$ | 0.1 | 30 or lower | 256 | 259 |
| 5 | $C_5H_{11}$ | $C_6H_{13}$ | 0.1 | 49 | — | 286 (Sm-I) |

EXAMPLE 6

Preparation of 4-pentyl-4'-[trans-4-(trans-4-pentylcyclohexyl)cyclohexyl]biphenyl (a compound of the formula (V) wherein R=R'=C₂H₅)

A solution of 4-pentyl-4'-bromobiphenyl (2.8 g, 0.0092 mol) dissolved in tetrahydrofuran (50 ml) was reacted with Mg (0.22 g, 0.0092 mol) in nitrogen current to obtain 4-pentyl-4'-biphenylmagnesium bromide. The reaction liquid was cooled to 0° C. and to this liquid was added a tetrahydrofuran solution (50 ml) of 4-pentylcyclohexylcyclohexanone (2.3 g, 0.0092 mol). The mixture was refluxed at 50° C. for 2 hours and 3N hydrochloric acid (50 ml) was then added, followed by extracting the product with toluene (200 ml), washing with water, distilling off the solvent, adding potassium hydrogen sulfate (4 g) and dehydrating at 200° C. for 2 hours in nitrogen atmosphere. After cooling, toluene (200 ml) was added and potassium hydrogen sulfate was filtered off, followed by washing with water till the washing water became neutral, dehydrating with anhydrous sodium sulfate, distilling off the solvent and recrystallizing from toluene to obtain crystals of 4-pentyl-4'-[4-(trans-4-pentylcyclohexyl)cyclohexen-1-yl]biphenyl. This product (1.4 g, 0.0031 mol) was dissolved in n-heptane (200 ml) and to the solution was added Raney Ni (0.7 g), followed by catalytic reduction under ordinary pressure at 60° C. The reaction was traced by gas chromatography, and when the raw material disappeared, that is, after 12 hours, reduction was completed. Since the resulting material was a mixture of cis-form and trans-form substances, it was recrystallized from toluene to take out the trans-form substance, that is, an objective product, 4-pentyl-4'-[trans-4-(trans-4-pentylcyclohexyl)cyclohexyl]-biphenyl. Yield: 0.5 g (0.001 mol). This product had such a very broad liquid-crystalline temperature range as a C-Sm point of room temperature or lower and a Sm-I point of 300° C. or higher.

EXAMPLE 7

Preparation of 4-ethyl-4'-[trans-4-(trans-4-pentylcyclohexyl)cyclohexyl]biphenyl (a compound of the formula (V) wherein R=C₅H₁₁ and R'=C₂H₅) (another method)

To metallic Mg (3.6 g, 0.148 mol) was dropwise added a solution of 4-bromobiphenyl (34.5 g, 0.148 mol) dissolved in tetrahydrofuran (100 ml), and the reaction temperature was kept at 35° C. in nitrogen current. After 2 hours, Mg dissolved to form a uniform solution, to which was dropwise added a solution of 4-(trans-4-pentylcyclohexyl)cyclohexanone (29.6 g, 0.118 mol) in tetrahydrofuran (100 ml) at 30° C. or lower under cooling, followed by refluxing for 2 hours, adding 3N hydrochloric acid (200 ml), extracting with toluene (1 l), washing with water and distilling off the solvent under reduced pressure to obtain a residue which was 4-[4-(trans-4-pentylcyclohexyl)cyclohexan-1-ol]-biphenyl.

To this material was added potassium hydrogen sulfate (7 g) and the material was dehydrated at 200° C. in nitrogen current, followed by cooling, dissolving it in toluene (1 l), filtering off potassium hydrogen sulfate, washing the toluene layer with water, distilling off the solvent under reduced pressure and recrystallizing from toluene to obtain crystals of 4-[4-(trans-4-pentylcyclohexyl)cyclohexen-1-yl]-biphenyl. To this material (14.0 g, 0.0362 mol) were added ethanol (300 ml) and Raney Ni (4.0 g), followed by reducing it under 5 Kg/cm² at 80° C. for 3 hours in an autoclave, filtering off the catalyst, washing with toluene and recrystallizing to obtain 4-[trans-4-(trans-4-pentylcyclohexyl)cyclohexyl]biphenyl. This material (2.0 g, 0.0052 mol) was dissolved in CS₂ (100 ml) and further anhydrous AlCl₃ (1.0 g, 0.0077 mol) was suspended, followed by dropwise adding acetyl chloride (0.42 g, 0.0054 mol) while the temperature was kept at 0°~10° C. After 1.5 hour, the temperature was gradually raised and reflux was carried out for 2 hours, followed by cooling, pouring the contents in 6N hydrochloric acid (500 ml), filtering the resulting solids and recrystallizing the solids from ethanol to obtain 4-acetyl-4'-[trans-4-(trans-4-pentylcyclohexyl)cyclohexyl]biphenyl. This material (1.7 g, 0.0039 mol) was dissolved in ethylene glycol (200 ml), and KOH (0.49 g) and hydrated hydrazine (0.52 g) were added, followed by refluxing for 4 hours, distilling off ethylene glycol, extracting with toluene (200 ml), washing with 6N hydrochloric acid, further washing with water till the washing water became neutral, distilling off toluene under reduced pressure and recrystallizing from fresh toluene to obtain an objective product, 4-ethyl-4'-[trans-4-(trans-4-pentylcyclohexyl)cyclohexyl]biphenyl (0.2 g), which had a C-Sm point of 68.0° C., a Sm-N point of 290° C. and a N-I point of 300° C. or higher.

EXAMPLES 8–11

Compounds of the formula (V) having different substituents were prepared in the same manner as in Example 6. Their phase transition points are shown in Table 2 together with the results of Examples 6 and 7.

TABLE 2

| Example | In formula (V) R | R' | Amount of Br—⟨⟩—⟨⟩—R' used (g) | Amount of R—⟨⟩—⟨⟩=O used (g) | Amount of R—⟨⟩—⟨⟩—⟨⟩—⟨⟩—R' used (g) | Yield (g) (mol) | Phase transition point (°C.) | |
|---|---|---|---|---|---|---|---|---|
| 8 | C₃H₇ | C₂H₅ | 12.8 | 8.0 | 5.4 (0.014 mol) | 0.9 (0.002 mol) | C—Sm Sm—N N—I | 71.4 279 300° C. or higher |
| 9 | C₄H₉ | C₂H₅ | 12.8 | 9.5 | 4.4 (0.011 mol) | 1.1 (0.0027 mol) | C—Sm Sm—I | 106.4 300° C. or higher |
| 7 | C₅H₁₁ | C₂H₅ | 12.8 | 10.0 | 2.0 (0.0048 mol) | 0.2 (0.0005 mol) | C—Sm Sm—N N—I | 68.0 290 300° C. or higher |
| 6 | C₅H₁₁ | C₅H₁₁ | 2.8 | 2.3 | 1.4 | 0.3 | C—Sm | room |

TABLE 2-continued

| Example | In formula (V) R | R' | Amount of Br-⬡-⬡-R' used (g) | Amount of R-⬢-⬢=O used (g) | Amount of R-⬢-⬡-⬡-R' used (g) | Yield (g) (mol) | Phase transition point (°C.) | |
|---|---|---|---|---|---|---|---|---|
| | | | | | (0.0031 mol) | (0.0007 mol) | Sm—I | temp. or lower 300° C. or higher |
| 10 | C₅H₁₁ | OCH₃ | 12.9 | 10.0 | 2.3 (0.0055 mol) | 0.4 0.001 mol | C—Sm Sm—N N—I | 87.2 260 300° C. or higher |
| 11 | C₅H₁₁ | OC₃H₇ | 18.8 | 17.5 | 2.2 (0.0049 mol) | 0.7 (0.0016 mol) | C—Sm Sm—I | 89.2 300° C. or higher |

EXAMPLE 12

Preparation of 4-ethyl-4'-(trans-4-ethylcyclohexyl)terphenyl (a compound of the formula (VI) wherein R and R' are each C₂H₅)

4-Ethyl-4'-[4'-(trans-4-ethylcyclohexyl)cyclohexen-1-yl]biphenyl (11 g, 0.030 mol) was dissolved in xylene (300 ml), and chloranil (16 g, 0.065 mol) was added, followed by reflux for 20 hours. After cooling, toluene (500 ml) was added, followed by washing once with 6N hydrochloric acid and three times with 2N NaOH, washing with saturated NaCl aqueous solution till the washing liquid became neutral, distilling off the solvent under reduced pressure, and recrystallizing from toluene to obtain an objective product, 4-ethyl-4'-(trans-4-ethylcyclohexyl)terphenyl (yield: 5 g) having a C-Sm point of 147.0° C. a Sm-N point of 260° C. and a N-I point of 300° C. or higher.

EXAMPLES 13-17

Other compounds of the formula (VI) prepared in the same manner as in Example 12 are shown in Table 3 together with the results of Example 12.

EXAMPLE 18

Preparation of 4-methyl-{4-[trans-4-(trans-4-ethylcyclohexyl)cyclohexyl]cyclohexen-1-yl}benzene (a compound of the formula (IV) wherein R is ethyl and R' is methyl)

Sliced Mg (1.2 g, 0.0049 mol) was placed in a three-neck flask, and a solution (30 ml) of 4-bromoanisole (9.2 g, 0.049 mol) dissolved in tetrahydrofurane was slowly dropwise added to the Mg in nitrogen current with stirring while the reaction temperature was kept at 30°~35° C., during which reaction proceeded and Mg dissolved in 3 hours to form a uniform solution of 4-methoxyphenylmagnesium bromide, to which a solution (50 ml) of 4-(trans-4-ethylcyclohexyl)-cyclohexanone (10.2 g, 0.049 mol) dissolved in tetrahydrofuran was dropwise added as rapidly as possible while the reaction temperature was kept at 5°~10° C. After the addition, the temperature was raised to 35° C., followed by stirring for 30 minutes, adding 3N hydrochloric acid (50 ml), placing the reaction liquid in a separating funnel, extracting three times with toluene (200 ml), washing combined toluene layers with water till the washing liquid became neutral and distilling off toluene under reduced pressure to obtain as an oily residue, 4-methoxy-[1-hydroxy-4-(trans-4-ethylcyclohexyl)cyclohexyl]benzene.

Potassium hydrogen sulfate (6 g) was added to it, followed by dehydrating at 160° C. for 2 hours in nitrogen current, cooling, adding toluene (200 ml), filtering

TABLE 3

| Example | In formula (VI) R | R' | Amount of R'-⬡-⬡-Br used (g) | Amount of R-⬢-⬢=O used (g) | Yield (g) | Phase transition point (°C.) C—Sm | Sm—N | N—I |
|---|---|---|---|---|---|---|---|---|
| 12 | C₂H₅ | C₂H₅ | 12.5 (0.049 mol) | 8.3 (0.040 mol) | 5.0 | 147.0 | 260 | 300< |
| 13 | C₂H₅ | C₅H₁₁ | 14.5 (0.049 mol) | 8.3 (0.040 mol) | 1.0 | room temp. or lower | 281 | 300< |
| 14 | C₄H₉ | H | 11.4 (0.049 mol) | 9.5 (0.040 mol) | 4.4 | 195.7 (C—N) | — | 235 |
| 15 | C₅H₁₁ | H | 11.4 (0.049 mol) | 10.0 (0.040 mol) | 2.7 | 134.7 | 261 | 284 |
| 16 | C₅H₁₁ | C₂H₅ | 12.5 (0.049 mol) | 10.0 (0.040 mol) | 4.0 | 91.1 | 294 | 300< |
| 17 | C₅H₁₁ | C₅H₁₁ | 14.5 (0.049 mol) | 10.0 (0.040 mol) | 3.0 | room temp. or lower | 300< | — | off potassium hydrogen sulfide, washing the toluene layer with water till the washing liquid became neutral, distilling off toluene under reduced pressure and recrystallizing the remaining oily substance from ethanol to obtain 4-methoxy-[4-(trans-4-ethylcyclohexyl)cyclohexen-1-yl]benzene. This material (70 g) was dissolved in ethanol (120 ml) together with Raney Ni catalyst (1.0 g) and subjected to catalytic reduction under ordinary pressure at 50° C. to absorb hydrogen (500 ml), followed by filtering off the catalyst and recrystallizing as it was. Since the resulting material was a mixture of cis-form and trans-form substances, it was further repeatedly recrystallized from ethanol to isolate the trans-form substance. The resulting 4-methoxy-[trans-4-(trans-4-ethylcyclohexyl)cyclohexyl]benzene (80 g) was dissolved in acetic acid (450 ml), and hydrobromic acid (47%) (450 ml) was added, followed by reflux for 30 hours. After the reaction the reaction liquid was cooled and crystals were deposited and filtered off, followed by recrystallizing the crystals from ethanol to obtain 4-hydroxy-[trans-4-(trans-4-ethylcyclohexyl)cyclohexyl]benzene. This material (20 g) was placed in an autoclave and ethanol (400 ml) was added and further Ru/C (3 g) was added to carry out catalytic reduction under 50 Kg/cm$^2$ at 180° C., followed by filtering off the catalyst and distilling off the solvent under reduced pressure to obtain 4-[trans-4-(trans-4-ethylcyclohexyl)cyclohexyl]cyclohexanol. To this material was added acetone (8 l), and a solution (50 ml) obtained by adding water to anhydrous chromic acid (14.5 g) and conc. sulfuric acid (23.6 g) was dropwise added over 2 hours while the temperature was kept at 0° C.~3° C. After completion of the reaction, an excess amount of the oxidant was decomposed by adding isopropyl alcohol, followed by further adding sodium hydrogen carbonate for neutralization, filtering off the resulting precipitate, washing it with acetone, combining the filtrate and the washing liquid together, distilling off acetone under reduced pressure, extracting three times with toluene (500 ml), drying combined toluene layers with sodium sulfate, distilling off toluene under reduced pressure, and recrystallizing from fresh toluene (50 ml) to obtain 4-[trans-4-(trans-4-ethylcyclohexyl)cyclohexyl]cyclohexanone (XII), which was then dried in vacuo on heating. This material (11.6 g) was dissolved in tetrahydrofuran (100 ml) and the solution was rapidly dropwise added to a solution of 4-methylbenzenemagnesium bromide obtained by reacting Mg piece (1.2 g) with p-bromotoluene (8.38 g). After reflux for 3 hours, the reaction liquid was cooled and 3N hydrochloric acid was added, followed by extracting with toluene (300 ml), repeating water-washing till the washing liquid became neutral, distilling off the solvent under reduced pressure, adding potassium hydrogen sulfate (4 g) to the remaining oily substance, dehydrating at 160° C. for 2 hours in nitrogen atmosphere, cooling, filtering off potassium hydrogen sulfate, adding toluene (300 ml), washing with water, distilling off the solvent under reduced pressure, and recrystallizing from fresh toluene (70 ml) to obtain an objective product, 4-methyl-{4-[trans-4-(trans-4-ethylcyclohexyl)cyclohexyl]cyclohexen-1-yl}benzene (yield: 4.6 g) having a C-Sm point of 59.4° C., a Sm-N point of 234° C. and a N-I point of 284° C.

EXAMPLE 19

Preparation of 4-methyl-{trans-4-[trans-4-(trans-4-ethylcyclohexyl)cyclohexyl]cyclohexyl}benzene (a compound of the formula (III) wherein R is ethyl and R' is methyl)

4-Methyl-{4-[trans-4-(trans-4-ethylcyclohexyl)cyclohexyl]cyclohexen-1-yl}benzene (3.2 g) was dissolved in toluene (300 ml) and Raney Ni catalyst (1.5 g) was added, followed by catalytic reduction under ordinary pressure at ordinary temperature. When the raw material disappeared through gas chromatography, the reaction finished. The solvent was distilled off and recrystallization from toluene was repeated to obtain 4-methyl-{trans-4-[trans-4-(trans-4-ethylcyclohexyl)cyclohexyl]cyclohexyl}benzene (yield: 0.8 g) having a C-Sm point of 71.0° C., a Sm-N point of 254° C. and a N-I point of 293° C.

EXAMPLE 20

Preparation of 4,4'-bis(4-propylphenyl)bicyclohexan-3,3'-diene (a compound of the formula (VIII) wherein R is propyl)

Mg piece (3.7 g, 0.15 mol) was reacted with 4-propylbromobenzene (30 g, 0.15 mol) in tetrahydrofuran at about 50° C. to obtain 4-propylbenzenemagnesium bromide, to which a solution of crystals of 4,4'-bicyclohexyldione (11.7 g, 0.06 mol) dissolved in tetrahydrofuran (200 ml) was added to obtain 4,4'-bis(4-propylphenyl)bicyclohexan-4,4'-diol. To this material was added potassium hydrogen sulfate (6 g), followed by dehydration at 200° C. for 2 hours in nitrogen current and recrystallization from toluene to obtain 4,4'-bis(4-propylphenyl)bicyclohexan-3,3'-diene (yield: 4.7 g) having a C-Sm point of 109.7° C., a Sm-N point of 243° C. and a N-I point of 259° C.

EXAMPLES 21 AND 22

Compounds having different substituents were prepared in the same manner as in Example 20. The values of their physical properties are shown in Table 4 together with the results of Example 20.

In addition the chemical structures of the compounds were confirmed by NMR, etc.

TABLE 4

| Example | R in formula (VIII) | Yield (g) | Yield (%)* | Phase transition point (°C.) | | |
|---|---|---|---|---|---|---|
| | | | | C-N (Sm) point | Sm-N point | N-I point |
| 20 | C$_3$H$_7$ | 4.7 | 20 | 109.7 | 243 | 259 |
| 21 | CH$_3$ | 47 | 27 | 198.7 ~199.0 | — | 263 |
| 22 | C$_3$H$_7$O | 38 | 17 | 151 | 251 ~253 | 283 |

*Values based on bicyclohexanedione

EXAMPLE 23

Preparation of trans,trans-4,4'-bis(4-propylphenyl)bicyclohexane (a compound of the formula (VII) wherein R is propyl)

(4-Propylphenyl)bicyclohexan-3,3'-diene (4.7 g) was dissolved in toluene (200 ml), and Raney Ni (2 g) was added, followed by subjecting to catalytic reduction under 3 Kg/cm$^2$ at 80° C. in an autoclave, stopping the reaction when disappearance of the raw material was observed by way of gas chromatography, filtering off the catalyst and recrystallizing to obtain an objective product, trans,trans-4,4'-bis(4-propylphenyl)bicyclohexane (VII) (yield: 1.3 g) having a C-Sm point of 104.7° C., a Sm-N point of 246° C. and a N-I point of 290° C.

EXAMPLES 24 AND 25

Compounds having different substituents were prepared in the same manner as in Example 23. The values of their physical properties are shown in Table 5 together with the results of Example 23.

In addition the chemical structures of the compounds were confirmed by way of NMR, etc.

TABLE 5

| Example | R in formula (VII) | Phase transition point (°C.) | | |
|---|---|---|---|---|
| | | C-N (Sm) point | Sm-N point | N-I point |
| 23 | $C_3H_7$ | 104.0 | 246 | 290 |
| 24 | $CH_3$ | 190.4~190.7 | — | 269 |
| 25 | $C_3H_7O$ | 158.1~159.0 | 245 | 300 or higher |

EXAMPLE 26

Preparation of 1,4-bis[4-(trans-4-propylcyclohexyl)-cyclohexen-1-yl]benzene (a compound of the formula (X) wherein R is propyl)

A solution of p-dibromobenzene (5.6 g, 0.024 mol) dissolved in tetrahydrofuran (200 ml) was dropwise added to sliced Mg (1.2 g, 0.049 mol) in nitrogen current so as to give soft reflux. After 7 hours, the reaction finished to yield its magnesium bromide, to which a solution of 4-(trans-4-propylcyclohexyl)-cyclohexanone (10.9 g, 0.049 mol) dissolved in tetrahydrofuran (100 ml) was rapidly dropwise added while the temperature was kept at 30° C. or lower. After the addition, the mixture was refluxed for 1.5 hour and 3N hydrochloric acid was added. The reaction liquid was extracted with toluene (100 ml×3), combined toluene layers were washed with water and the solvent was distilled off under reduced pressure. The remaining oily substance was 1,4-bis[4-(trans-4-propylcyclohexyl)-cyclohexan-1-ol]benzene, to which potassium hydrogen sulfate (2.5 g) was added, followed by dehydrating at 200° C. for 2 hours in nitrogen current, cooling, adding toluene (300 ml), filtering off potassium hydrogen sulfate, washing toluene layer with water, distilling off the solvent under reduced pressure and recrystallizing the residue from toluene to obtain an objective product, 1,4-bis[4-(trans-4-propylcyclohexyl)cyclohexen-1-yl]benzene (yield: 0.9 g) having a C-Sm point of 98.5° C. and a Sm-I point of 300° C. or higher.

EXAMPLE 27

Example 26 was repeated except that 4(trans-4-propylcyclohexyl)cyclohexanone in Example 26 was replaced by 4-(trans-4-pentylcyclohexyl)cyclohexanone, to prepare 1,4-bis[4-(trans-4-pentylcyclohexyl)cyclohexen-1yl]benzene (C-Sm point: 47.7° C., Sm-I point: 300° C. or higher).

EXAMPLE 28

Preparation of 1,4-bis[trans-4-(trans-4-propylcyclohexyl)cyclohexyl]benzene (a compound of the formula (IX) wherein R is propyl)

Raney Ni catalyst (0.5 g) was added to a solution of 1,4-bis[4-(trans-4-propylcyclohexyl)cyclohexen-1-yl]benzene (0.9 g) dissolved in toluene (70 ml), followed by subjecting to catalytic reduction at ordinary temperature under ordinary pressure, tracing the reaction by gas chromatography and stopping the reaction when the raw material disappeared. Since the product was a mixture of cis-form and trans-form substances, it was recrystallized from toluene to obtain an objective product, 1,4-bis[trans-4-(trans-4-propylcyclohexyl)cyclohexyl]benzene (yield: 0.3 g, C-Sm point: room temperature or lower, Sm-I point: 300° C. or higher).

EXAMPLE 29

Example 28 was repeated except that 4-(trans-4-propylcyclohexyl)cyclohexanone was replaced by 4-(trans-4-pentylcyclohexyl)cyclohexanone, to prepare 1,4-bis[trans-4-(trans-4-propylcyclohexyl)cyclohexyl]benzene (C-Sm point: 47.7° C., Sm-I point: 300° C. or higher).

EXAMPLE 30 (APPLICATION EXAMPLE 1)

A liquid-crystalline composition (A) consisting of trans-4-propyl-(4'-cyanophenyl)cyclohexane 28%, trans-4-pentyl-(4'-cyanophenyl)cyclohexane 43% and trans-4-heptyl-(4'-cyanophenyl)cyclohexane 29% has a N-I point of 52° C., a dielectric anisotropy value $\Delta\epsilon$ of +10.5, a threshold voltage of 1.53 V and a saturation voltage of 2.12 V relative to a TN cell having the composition sealed therein, a viscosity at 20° C. of 23 cp and an optical anisotropy value $\Delta n$ of 0.12.

When 1-(trans-4-ethylcyclohexyl)-4-[trans-4-(trans-4-propylcyclohexyl)cyclohexyl]benzene (5 parts) obtained in Example 3 of the present invention was added to the above liquid crystal mixture (95 parts), the resulting liquid-crystalline composition had a raised N-I point of 60.5° C., a $\Delta\epsilon$ of +10.6, a threshold voltage of 1.70 V, a saturation voltage of 2.5 V relative to a TN cell having this composition sealed therein and a viscosity at 20° C. of 30.3 cp.

Thus, it is seen that addition of the compound of the present invention in a small amount is effective for broadening the nematic temperature range.

EXAMPLE 31 (APPLICATION EXAMPLE 2)

When 4-pentyl-4'-[trans-4-(trans-4-pentylcyclohexyl)-cyclohexyl]biphenyl of Example 6 as a compound of the present invention (2 parts) was added to the above liquid-crystalline composition (A) (98 parts), the resulting liquid-crystalline composition had a raised N-I point of 56.2° C., a $\Delta\epsilon$ of +11.0, a threshold voltage of 1.55 V, a saturation voltage of 2.15 V and a viscosity at 20° C. of 24.9 cp.

Thus, it is seen that addition of the compound of the present invention in a small amount is effective for preparing a composition having a low viscosity and a broad nematic temperature range.

EXAMPLE 32 (APPLICATION EXAMPLE 3)

When 4-ethyl-4'-(trans-4-pentylcyclohexyl)terphenyl of Example 16 of the present invention (5 parts) was added to the above liquid-crystalline composition (A) (95 parts), the resulting liquid-crystalline composition had a raised N-I point of 61.5° C., a threshold voltage of 1.62 V, a saturation voltage of 2.44 V, a viscosity at 20° C. of 24.8 cp and a raised Δn of 0.126. Thus it is seen that addition of the compound of the present invention in a small amount is effective for preparing a composition having a low viscosity and a broad nematic temperature range.

EXAMPLE 33 (APPLICATION EXAMPLE 4)

When 4-methyl-{4-[trans-4-(trans-4-ethylcyclohexyl)-cyclohexyl]cyclohexen-1-yl}benzene of Example 18 of the present invention (5 parts) was added to the above liquid-crystalline composition (A) (95 parts), the resulting liquid-crystalline composition had a raised N-I point of 61.9° C., a threshold voltage of 1.6 V, a saturation voltage of 2.2 V and a viscosity at 20° C. of 25 cp. Thus it was possible to obtain a liquid-crystalline composition having a low viscosity and a broad nematic temperature range.

EXAMPLE 34 (APPLICATION EXAMPLE 5)

When 4-methyl-{trans-4-[trans-4-(trans-4-ethylcyclohexyl)cyclohexyl}benzene of Example 19 of the present invention (5 parts) was added to the above liquid-crystalline composition (A) (95 parts), the resulting liquid-crystalline composition had a raised N-I point of 61.5° C.; its viscosity at 20° C. was 25 cp, that is, did not rise so much; the threshold voltage and saturation voltage were 1.5 V and 2.1 V, respectively; thus it was possible to broaden the nematic temperature range without raising these voltages.

EXAMPLE 35 (APPLICATION EXAMPLE 6)

When 4,4'-bis(4-propylphenyl)bicyclohexan-3,3'-diene of Example 20 of the present invention (2.5 parts) was added to the above liquid-crystalline composition (A) (97.5 parts), the resulting liquid-crystalline composition had a raised N-I point of 56.4° C., a viscosity at 20° C. of 26.1 cp, a threshold voltage of 1.58 V and a saturation voltage of 2.15 V. Thus addition of the compound of the present invention in a small amount made it possible to broaden the nematic temperature range without raising the viscosity so much.

EXAMPLE 36 (APPLICATION EXAMPLE 7)

When trans,trans-4,4'-bis(propylphenyl)bicyclohexane of Example 23 of the present invention (5 parts) was added to the above liquid-crystalline composition (A) (95 parts), the resulting liquid-crystalline composition had a raised N-I point of 59.1° C., a viscosity at 20° C. of 24.9° C., a threshold voltage of 1.64 V and a saturation voltage of 2.27 V. Thus addition of the compound of the present invention made it possible to broaden the nematic temperature range without raising the viscosity so much.

EXAMPLE 37 (APPLICATION EXAMPLE 8)

A liquid-crystalline composition consisting of trans-4-propyl-(4'-cyanophenyl)cyclohexane 25.5%, trans-4-pentyl-(4'-cyanophenyl)cyclohexane 34.0%, trans-4-heptyl-(4'-cyanophenyl)cyclohexane 25.5% and trans-4-pentyl-(4-cyanobiphenyl)cyclohexane 15.0% has a nematic liquid-crystalline temperature range of −6° C. ~ +72.3° C., a viscosity at 20° C. of 27.6 cp, a dielectric anisotropy value Δε of 11.5, and a TN cell having the composition sealed therein has a threshold voltage of 1.69 V and a saturation voltage of 2.45 V.

When 1,4-bis[4-(trans-4-propylcyclohexyl)cyclohexen-1-yl]benzene of Example 26 of the present invention (one part) was added to the above composition (99 parts), the resulting liquid-crystalline composition had a broadened nematic temperature range of −6° C. ~ +75.0° C., a viscosity at 20° C. of 31 cp, a dielectric anisotropy of +10.9, and a TN cell having this composition sealed therein had a threshold voltage of 1.71 V and a saturation voltage of 2.4 V.

EXAMPLE 38 (APPLICATION EXAMPLE 9)

When 1,4-bis[trans-4-(trans-4-pentylcyclohexyl)-cyclohexyl]benzene of Example 29 of the present invention (2 parts) was added to the above composition (A) (98 parts, the resulting liquid-crystalline composition had a raised N-I point of 56.7° C., a Δε of +10.8, a threshold voltage of 1.54 V and a saturation voltage of 2.1 V relative to a TN cell having this composition sealed therein, and a viscosity at 20° C. of 26 cp. Thus addition of the compound of the present invention in a small amount is effective for broadening the nematic temperature range.

What is claimed is:

1. Compounds selected from the group consisting of

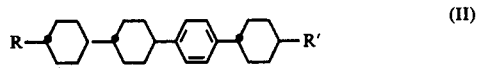
(II)

wherein R and R' represent hydrogen atom or an alkyl group of 1 to 10 carbon stoms, respectively;

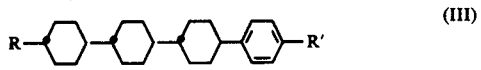
(III)

wherein R and R' represent hydrogen atom or an alkyl group or an alkoxy group, each of 1 to 10 carbon atoms, respectively;

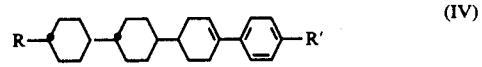
(IV)

wherein R and R' represent hydrogen atom or an alkyl group or an alkoxy group, each of 1 to 10 carbon atoms, respectively;

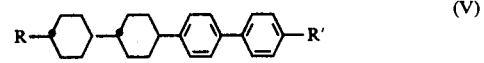
(V)

wherein R and R' represent hydrogen atom or an alkyl group or an alkoxy group, each of 1 to 10 carbon atoms, respectively;

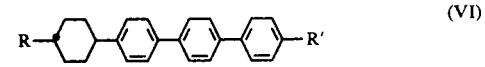
(VI)

wherein R and R' represent hydrogen atom or an alkyl group or an alkoxy group, each of 1 to 10 carbon atoms, respectively;

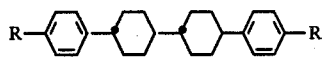 (VII)

wherein R represents hydrogen atom or an alkyl group or an alkoxy group, each of 1 to 10 carbon atoms, but the number of hydrogen atoms cannot exceed one;

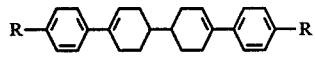 (VIII)

wherein R represents hydrogen atom or an alkyl group or an alkoxy group, each of 1 to 10 carbon atoms;

 (IX)

wherein R and R' represent hydrogen atom or an alkyl group of 1 to 10 carbon atoms, respectively; and

 (X)

wherein R and R' represent hydrogen atom or an alkyl group of 1 to 10 carbon atoms, respectively.

2. 1-(Trans-4-alkylcyclohexyl)-4-[trans-4-(trans-4-alkylcyclohexyl)cyclohexyl]benzenes expressed by the general formula

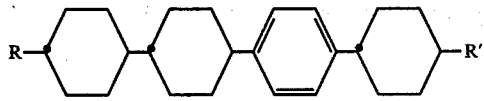

wherein R and R' each represent hydrogen atom or an alkyl group of 1 to 10 carbon atoms.

3. 4-Substituted-{trans-4-[trans-4-(trans-4-alkylcyclohexyl)cyclohexyl]cyclohexyl}benzenes expressed by the general formula

wherein R and R' each represent hydrogen atom or an alkyl group or an alkoxy group, each of 1 to 10 carbon atoms.

4. 4-Substituted-{4-[trans-4-(trans-4-alkylcyclohexyl)-cyclohexyl]cyclohexen-1-yl}benzenes expressed by the general formula

wherein R and R' each represent hydrogen atom or an alkyl group or an alkoxy group, each of 1 to 10 carbon atoms.

5. 4-Substituted-4-[trans-4-(trans-4-substituted-cyclohexyl)cyclohexyl]biphenyls expressed by the general formula

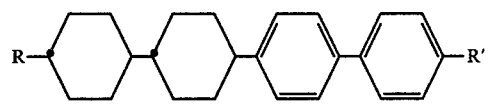

wherein R and R' each represent hydrogen atom or an alkyl group or an alkoxy group, each of 1 to 10 carbon atoms.

6. 4-Substituted-4'-(trans-4-alkylcyclohexyl)-terphenyls expressed by the general formula

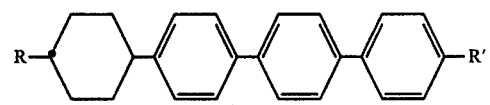

wherein R and R' each represent hydrogen atom or an alkyl group or an alkoxy group, each of 1 to 10 carbon atoms.

7. Trans,trans-4,4'-bis(4-substituted-phenyl)-bicyclohexanes expressed by the general formula

wherein R represents hydrogen atom or an alkyl group or an alkoxy group, each of 1 to 10 carbon atoms but the number of hydrogen atoms cannot exceed one.

8. 4,4'-Bis(4-substituted-phenyl)bicyclohexan-3,3'-dienes expressed by the general formula

wherein R represents hydrogen atom or an alkyl group or an alkoxy group, each of 1 to 10 carbon atoms.

9. 1,4-Bis[trans-4-(trans-4-alkylcyclohexyl)cyclohexyl]-benzenes expressed by the general formula

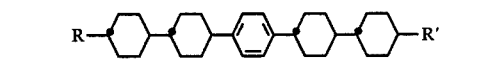

wherein R and R' each represent hydrogen atom or an alkyl group of 1 to 10 carbon atoms.

10. 1,4-Bis[4-(trans-4-alkylcyclohexyl)cyclohexen-1-yl]benzenes expressed by the general formula

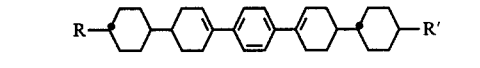

wherein R and R' each represent hydrogen atom or an alkyl group of 1 to 10 carbon atoms.

11. A liquid crystal composition comprising a mixture of compounds at least one of which is a compound as set forth in claim 1.

12. A liquid crystal composition comprising a mixture of compounds at least one of which is a compound set forth in claim 2.

13. A liquid crystal composition comprising a mixture of compounds at least one of which is a compound as set forth in claim 3.

14. A liquid crystal composition comprising a mixture of compounds at least one of which is a compound as set forth in claim 4.

15. A liquid crystal composition comprising a mixture of compounds at least one of which is a compound as set forth in claim 5.

16. A liquid crystal composition comprising a mixture of compounds at least one of which is a compound as set forth in claim 6.

17. A liquid crystal composition comprising a mixture of compounds at least one of which has the formula set forth in claim 7 and wherein R represents a hydrogen atom or an alkyl group or an alkoxy group, each of 1 to 10 carbon atoms.

18. A liquid crystal composition comprising a mixture of compounds at least one of which is a compound as set forth in claim 8.

19. A liquid crystal composition comprising a mixture of compounds at least one of which is a compound as set forth in claim 9.

20. A liquid crystal composition comprising a mixture of compounds at least one of which is a compound as set forth in claim 10.

* * * * *